United States Patent [19]

Cartmell

[11] Patent Number: 4,832,036
[45] Date of Patent: May 23, 1989

[54] MEDICAL ELECTRODE

[75] Inventor: James V. Cartmell, Dayton, Ohio

[73] Assignee: Baxter International Inc., Deerfield, Ill.

[21] Appl. No.: 733,521

[22] Filed: May 13, 1985

[51] Int. Cl.⁴ ............................................. A61B 5/04
[52] U.S. Cl. .................................... 128/640; 128/802
[58] Field of Search .......................... 128/637–641, 128/644, 798, 802, 803

[56] References Cited

U.S. PATENT DOCUMENTS

| | | |
|---|---|---|
| 3,085,577 | 4/1963 | Berman et al. . |
| 3,357,930 | 12/1967 | Marks . |
| 3,565,055 | 2/1971 | Amoroso .............................. 128/174 |
| 3,565,059 | 2/1971 | Hauser et al. . |
| 3,580,240 | 5/1971 | Cosentino . |
| 3,599,629 | 8/1971 | Gordy .................................. 128/640 |
| 3,607,788 | 9/1971 | Adolph et al. ....................... 128/252 |
| 3,746,004 | 7/1973 | Jankelson . |
| 3,828,766 | 8/1974 | Krasnow . |
| 3,993,049 | 11/1976 | Kater . |
| 3,998,215 | 12/1976 | Anderson et al. . |
| 4,016,869 | 4/1977 | Reichenberger ..................... 128/252 |
| 4,040,412 | 8/1977 | Sato . |
| 4,050,453 | 9/1977 | Castillo et al. . |
| 4,051,842 | 10/1977 | Hazel et al. . |
| 4,066,078 | 1/1978 | Berg . |
| 4,067,342 | 1/1978 | Burton . |
| 4,109,648 | 8/1978 | Larke et al. . |
| 4,125,110 | 11/1978 | Hymes .................................. 128/260 |
| 4,126,126 | 11/1978 | Bare et al. ........................... 128/339 |
| 4,141,366 | 2/1979 | Cross, Jr. et al. . |
| 4,155,354 | 5/1979 | Rasmussen . |
| 4,239,046 | 12/1980 | Ong ..................................... 128/640 |
| 4,243,051 | 1/1981 | Wittemann ......................... 128/802 |
| 4,243,052 | 1/1981 | Bailey .................................. 128/802 |
| 4,274,420 | 6/1981 | Hymes . |
| 4,300,575 | 11/1981 | Wilson ................................ 128/798 |
| 4,304,235 | 12/1981 | Kaufman ............................ 128/798 |
| 4,317,278 | 3/1982 | Cunn et al. ......................... 128/639 |
| 4,319,579 | 3/1982 | Cartmell . |
| 4,370,984 | 2/1983 | Cartmell ............................. 128/640 |
| 4,387,714 | 6/1983 | Geddes et al. ...................... 128/798 |
| 4,401,125 | 8/1983 | Taylor et al. ....................... 128/639 |
| 4,409,981 | 10/1983 | Lundberg . |
| 4,418,697 | 12/1983 | Tama . |
| 4,524,087 | 6/1985 | Engel .................................. 128/641 |

FOREIGN PATENT DOCUMENTS

| | | |
|---|---|---|
| 8500017 | 1/1985 | PCT Int'l Appl. ................ 128/802 |
| 1519782 | 8/1978 | United Kingdom . |

Primary Examiner—Max Hindenburg
Attorney, Agent, or Firm—Roger S. Dybvig

[57] ABSTRACT

In contrast to the usual practice of bridging a medical electrode conductor to the skin of a patient by way of an interposed electrolyte, the present invention interposes the medical electrode conductor between the skin and an electrolyte which is larger in area than the interposed conductor.

28 Claims, 2 Drawing Sheets

MEDICAL ELECTRODE

BRIEF SUMMARY OF THE INVENTION

In contrast to the common technique of interposing an electrolyte means between the skin of a patient and an electrocardiograph electrode conductor, the present invention partially reverses this arrangement by interposing the electrode conductor between the skin of a patient and the electrolyte means. Also in the present invention the electrolyte means comprises an adhesive rendered conductive by the inclusion of an electrolytic salt. The arrangement of the electrode is such that the conductive adhesive may engage only a small portion of metallic conductor while also engaging a larger portion of the patient's skin. The primary signal path for electrocardiographic signals proceeds from the heart to the patient's skin, then to the conductive adhesive means lying on the patient's skin, to the metallic conductor lying under the conductive adhesive means, and then to an insulated lead wire connecting the metallic conductor to a monitoring instrument. A cover means covering the conductive adhesive means and coated with an adhesive on one face thereof anchors the lead wire so as to minimize disturbance to the electrical signal sought to be monitored. Such cover means further protects the conductive adhesive means from adhesion to the clothing or bedding of a patient to whom the electrode has been applied.

DETAILED DESCRIPTION

Figure 1:
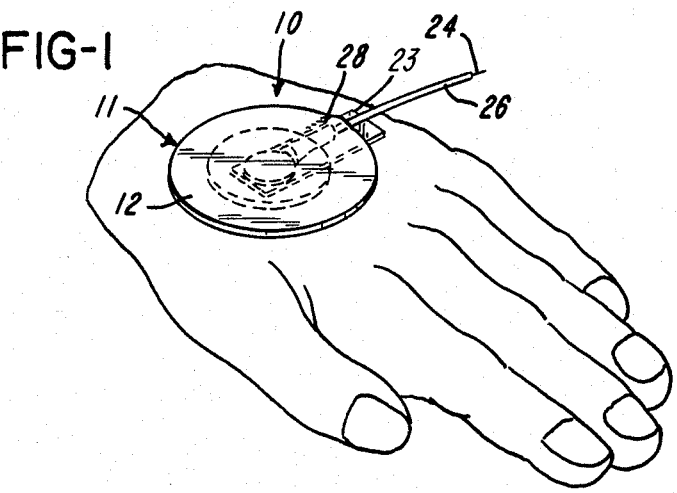
FIG. 1 is a perspective illustration of the electrode of the present invention attached to the hand of a patient, with the electrode lead wire having been broken away and with an optional insulator included.

Referring to the drawings in greater detail, the electrode of the present invention has been designated generally with the reference number 10. The electrode 10 includes a cover means 11 comprising a closed cell foam pad 12 and a layer of pressure sensitive adhesive 14 covering one face of the foam pad 12. The foam pad 12 may comprise any of a wide variety of thermoplastic foams which are well known in the art. However, the material of choice for the present invention is a polyethylene foam.

In the drawings, the foam pad 11 is shown as having a circular shape. However, the shape is ordinarily a mere matter of convenience and thus the pad 12 may have other shapes.

Placed centrally on the layer 14 so as to be spaced from the edges of such layer, and thus to define thereabout a margin 18, is a matrix 16 of a conductive adhesive. Various conductive adhesive materials may be used depending upon the application for which the electrode is intended. The material of choice for the present application is a urethane hydrogel. Alternate materials include a commercially available conductive adhesive composition comprising karaya gum modified with sodium chloride, available from LecTec Corporation, 120 South Crosstown Circle, Eden Prairie, Minn. Various other conductive adhesive compositions are described in the following United States Patents: Marks et al. U.S. Pat. No. 3,357,930; Kater U.S. Pat. No. 2,993,049; Berg U.S. Pat. No. 4,066,076; Hymes U.S. Pat. No. 4,125,110; Cross et al. U.S. Pat. No. 4,141,366; and Hymes U.S. Pat. No. 4,274,420.

Whatever the composition of the conductive adhesive, it should be of the type which will adhere to the skin of a patient and will have a cohesive strength sufficient to permit the conductive adhesive to be peeled from the skin to which it is attached without leaving any appreciable residue.

It is convenient to refer to the cover means 11, including the foam pad 12 and the adhesive layer 14 to which the conductive adhesive matrix is added, as a disposable part of the electrode being described. The size of the pad 12 is not a critical aspect of the present invention but, for convenience, the diameter of the pad 12 may be approximately two inches, with the diameter of the conductive adhesive matrix ultimately applied thereto being approximately 1¼ inches. Thus, the disposable part of the electrode is of a size readily wrapped about small limbs, such as babies' limbs, but this wrap-around feature is not a major consideration since a large number of applications for electrodes of the type being described will involve applications of the electrodes to large surfaces, such as the chest or leg of an adult.

The surface area of the conductive adhesive matrix is also not critical to the present invention. However, since the conductive adhesive matrix will include and thus be acting as an electrolyte, one would desire the area of the conductive adhesive matrix to be as large as will be convenient.

Figure 2:
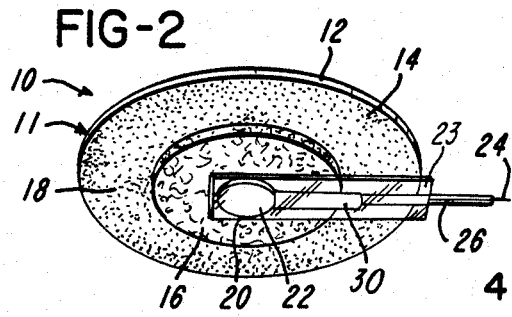
FIG. 2 is a perspective illustration showing the opposite face of the electrode after removal from the patient's skin with the electrode lead wire having again been broken away and also showing the optional insulator.

FIG. 2 illustrates an electrode conductor comprising a plate 20 having an integrally formed, outwardly projecting strip. In FIG. 2 the strip is not visible because surrounded by a shrink-fitted sleeve 30. Also, not appearing in FIG. 2, is a soldered junction whereby a lead wire 24 is soldered to the strip surrounded by the sleeve 30. The purpose of shrink-fitting the sleeve 30 covering the soldered junction is to exclude from that junction any of the conductive adhesive electrolyte that will be permitted to contact the plate 20.

The plate 20 and its lead wire connection can be conveniently referred to as a reusable part of the electrode since the conductor plate 20 and its lead wire may be used over and over again, with each new use ordinarily requiring attachment to a new disposable assembly such as already described.

Figure 3:
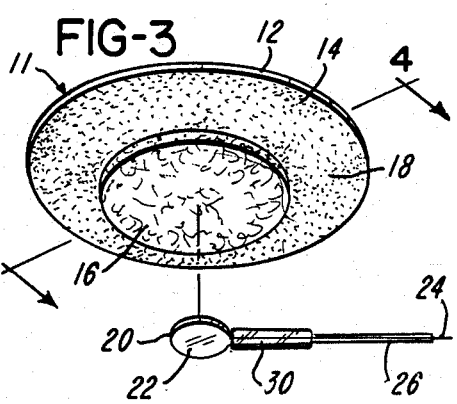
FIG. 3 is a perspective illustration of the present invention wherein a reusable conductor assembly has been exploded away from a disposable portion of the electrode, the lead wire having again been broken away.
Figure 4:
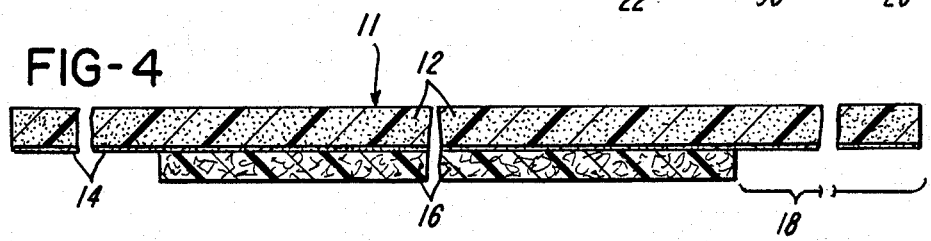
FIG. 4 is an enlarged sectional illustration of the disposable portion of the electrode, the section having been taken substantially along the line 4—4 of the FIG. 3 and portions having been broken away.

The plate 20 and its outwardly extending strip, before soldered to the lead wire 24, are preferably smooth over their opposite faces and comprise preferably a thin sheet of silver whose exposed surfaces 22 are chlorided. The electrolyte included in the conductive adhesive matrix used in the electrode of the present invention should be tailored to the metallic character of the conductor 20, 22. The preferred conductor described is a chlorided silver conductor for which sodium chloride forms a compatible electrolyte. Should the conductor be stainless steel, for example, it would then be preferred that the electrolyte comprise a sulphate gel. Other variations in the nature of the electrolyte employed will occur to those skilled in the art. Alternatively the plate 20 and its outwardly extending strip could be a plastic coated with silver chloride or a plastic produced by adding silver chloride powder to a binder so as to create a paint which can serve as the conductor plate. In the particular conductor arrangement illustrated in FIGS. 2 and 3, the chlorided conductor is attached by solder to a less noble lead wire 24, such as a copper wire surrounded by conventional insulation 26. In those cases where the plate 20 and its outwardly extending strip comprise a plastic containing dispersed silver chloride or coated with a silver chloride, the lead wire 24 is crimped upon or otherwise secured in contact with the plastic part.

In the use of the electrode being described, the chlorided silver conductor 20 is placed at any convenient located on the skin of the patient to be examined or treated, and then the conductive adhesive matrix laid over the conductor so as to sandwich the conductor between the conductive adhesive matrix 16 and the skin of the patient to be examined or treated. In this regard, it is to be noted that the size of the conductor 20 is small in relation to the overlying surface area of the conductive adhesive matrix and this allows the surrounding or outlying portions of that matrix to adhere to the patient's skin. At the same time the adhesive 14, exposed at the margin 18, is brought into adhesive contact with the patient's skin. The electrode attachment thus supports the cover means 11 in such position that the matrix is covered by the cover means 11. The lead wire 24 along with the sheath 30 accordingly pass outwardly under the matrix 16 and over the patient's skin for attachment to peripheral equipment. As illustrated in FIGS. 1 and 2, some users of the medical electrode being described may prefer to insert between the conductor 20 and the patient's skin a thin sheet 23, comprising a plastic or the like, to assure that none of the signal passing through the matrix 16 is being compromised by direct contact between the conductor plate 20 and the skin of the patient. The insulator 23, as is shown, is narrow in relation to its length so that a maximal area of the matrix 16 will be permitted to engage the patient's skin. The insulator, when used, extends parallel to the lead wire 24 from the region of the conductor plate 20 to a position which is outside the perimeter of the foam pad 12, as is shown.

The electrode is ordinarily used with no or at least minimal skin preparation. Thus, the conductive adhesive matrix is contacted to the epidermis, which is ordinarily a poor electrical conductor. However, since the conductive adhesive matrix is a hydrogel and thus preponderantly water bound in a gelatinous medium, the conductive adhesive matrix engages the skin so as to establish a relatively good electrical contact to the skin. In contrast, the chlorided silver surface of the conductor plate 20 makes a relatively poor electrical connection to the patient's epidermis.

It can be noted that the conductive adhesive matrix 16 has three surface areas of importance. The first area is determined by that surface or side of the conductive adhesive matrix which engages the cover means 11. The second area of importance is that relatively small area of the opposite side which lies against the plate 20. The third area comprises the balance of the opposite side which will, in use, adhere to the skin of the patient. The importance of the first area has to do with its adhesion to the cover means 11 and its cohesive strength. The adhesion to the cover means 11 is determined primarily by the adhesive layer 14. The importance of the second area has to do with the ability of the conductive adhesive matrix to peel cleanly with minimal residue from the plate 20 and with the efficiency with which electrocardiographic signals pass between the conductive adhesive matrix and the plate 20. The importance of the third area has to do with its adhesion to the skin of a patient and its ability to peel away from such skin without leaving a residue. The surface of the cover means 11 opposite the surface covered by the pressure sensitive adhesive layer 14 is free of tack. Thus, the electrode is easily peeled from the patient's skin and its disposable portion discarded.

Bearing in mind that the area of contact between the conductive adhesive matrix and the skin is much greater than the area of contact between the plate 20 and the skin, the clearly preferred signal path between the skin and the wire 24 proceeds from the skin through the conductive adhesive matrix to the plate 20, with the direct path from the skin to the plate 20 being less favorable, owing to the relatively small area of skin contact and the relative deficiency of ions at the epidermal skin surface. While the relatively poor conductivity between the patient's skin and the plate 20 allows one to place the plate 20 directly against the patient's skin, it is sometimes convenient to insert any thin insulating sheet between the plate 20 and the patient's skin, thus to prevent any compromise of electrocardiograph signals being sensed with the aid of the plate 20. Such a thin insulating sheet is identified by the reference number 23 in FIGS. 1 and 2.

In the preferred form of the present invention, the insulation 26 surrounding the wire 24 lies between the patient's skin and the adhesive layer 14 with the foam pad 12, when pressed against the skin of the patient, forming a bulge 28 as it partially wraps over the insulation 26.

In the absence of the optional insulator 23, it is to be noted that the adhesive layer 14 has been used to serve two functions. The primary function was to attach the electrode to the skin of the patient. An important secondary function is to anchor the conductor 24 against the skin of the patient. Such anchoring stabilizes the conductor with respect to the patient's skin and minimizes the occurrence of distortions or artifacts which could disturb the electrocardiograph signal sought to be monitored and recorded. The cover means 11 will also serve to some extent to retard evaporation of moisture from the conductive adhesive matrix 16. When an insulator, such as the insulator 23, is being used, the ability of the adhesive layer 14 to anchor the conductor 24 against the skin of the patient may be reduced due to the presence of the insulator 23. However, the matrix 16, because engaged with the conductor 20 and with the lead wire, adequately supplements the anchoring capabilities of the electrode assembly being described.

Figure 5:
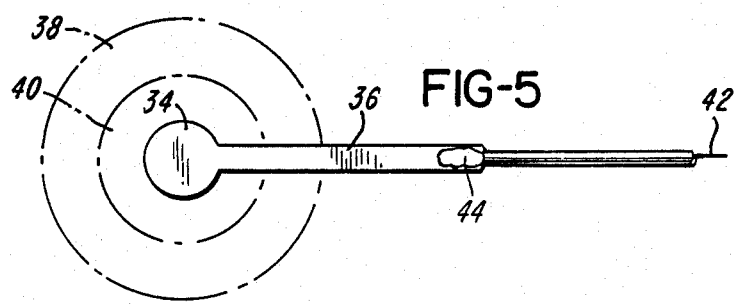
FIG. 5 is a plan view illustrating a first modification of the reusable portion of the electrode and illustrating with broken lines the size relationship between the modified reusable portion and the disposable portion.

FIG. 5 illustrates a modification of the present invention wherein the need for a shrink-fitted sleeve is eliminated by so shaping the conductor 34 that a strip 36, which is an integral part of the conductor 34, can project outwardly from the disposable conductive adhesive matrix sufficiently to extend beyond the peripheral edges of its covering pad. FIG. 5 shows the modified conductor 34 with its strip 36 in solid lines. Shown in phantom behind the conductor 34 and strip 36 is the shape of a disposable electrode assembly comprising a pad 38 supporting a matrix 40 of conductive adhesive. The pad 38 and conductive adhesive matrix 40 are shown in phantom lines behind the modification being illustrated in FIG. 5 simply to illustrate the size relationship between the conductor 34 and its outwardly extending strip 36 in relation to the disposable part that would normally in use lie against the backside of the conductor 34. Thus, FIG. 5 illustrates with solid lines a conductor 34 having one piece therewith the integrally formed strip 36. As illustrated in FIG. 5, the strip 36 may be secured by a solder 44 to a lead wire 42. Since the solder is located remotely from any conductive adhesive matrix, there is no concern that conductive adhesive will contact the soldered joint and, thus, no concern over the development of offset voltages due to battery action.

The description of the modification appearing in FIG. 5 suggests immediately to one skilled in the art that by a thoughtful shaping of the electrode conductor and attention to the location of the conductive adhesive matrix contacted thereby, there can be many conductor configurations in which the shrink-fitted sleeve described in reference to the preferred embodiment can be omitted.

The electrode devices illustrated in FIGS. 1 through 5 of the present application utilize an electrode conductor which, when the optical insulator 23 is omitted and the electrode is being used, may lie against the skin of the patient with there being a general reliance on the low conductivity of the outer surface of the patient's skin to prevent compromise or distortion of a signal sought to be monitored.

Figure 6:
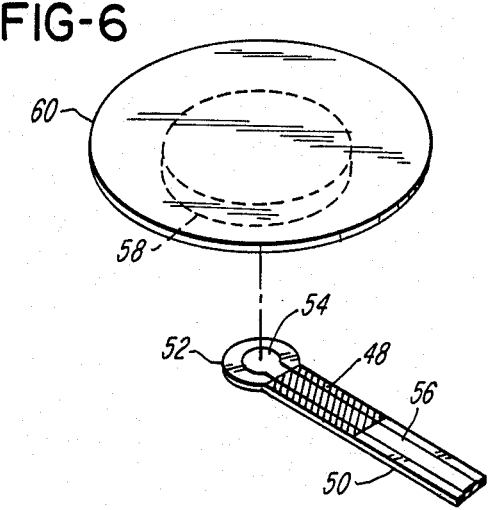
FIG. 6 is a perspective illustration of a second modification of the present invention wherein a reusable conductor assembly has been exploded away from a disposable portion of the electrode, a part of the reusable portion having been broken away.

In the embodiment of FIG. 6 a printed circuit conductor of the type already illustrated in U.S. Pat. No. 4,257,424, issued Mar. 24, 1981 to the herein identified inventor, may be employed. Such a printed circuit conductor is illustrated in FIG. 6 with the conductor comprising an elongate sheet 50 having an enlarged circular head 52.

Sheet 50 comprises an insulating material which may be polyethylene terephthalate as one example, onto which has been painted a layer 54 having a shape similar to that of the insulator 50 but of size smaller than the insulator 50. The painted layer 54 may comprise conductive paintable material such as DuPont Conductor Composition No. 9793, a conductive silver paint tailored for screen printing electrical circuits onto plastic substrates.

Painted or otherwise applied to the sheet 50 and in overlying relationship to a length of the painted layer 54 is a barrier layer 48 comprising a nonconductive moisture impermeable material such as an acrylic plastic or the like. Barrier layer 48 protects a length of the painted layer 54 from contact with the conductive adhesive as will be described.

As described, the structure of FIG. 6 employs a polyethylene terephthalate insulator. The reference number 58 schematically illustrates the conductive adhesive matrix. This matrix is adhesively tacked to the under surface of a protective cover 60 which is analogous to the cover means 11 previously described. The size of the matrix 58 is such that the matrix, when applied centrally onto the enlarged head 52, will lie on the barrier layer 48 without lapping onto the bare extension 56 of the painted layer 54. The bare extension 56 is thus protected from chemical interaction with the conductive adhesive matrix 58 with the bare extension 56 providing a suitable point of attachment to peripheral equipment.

In operation the conductive adhesive matrix 58 is laid onto the enlarged head 52 with surrounding portions of the conductive adhesive intimately contacting the skin of the patient. Electrical signals such as electrocardiograph signals thus proceed from the skin through the conductive adhesive to the painted layer 54. The signals available at the painted layer 54 are picked up by conventional wire elements, not shown, which are engaged to the extension 56. Since the electrical signals will be picked up remotely from the conductive adhesive matrix, there will be no likelihood that the signal being picked up will be compromised by offset voltages or other artifacts. It can be noted, of course, that the polyethylene terephthalate sheet 50 separates the painted silver layer from the patient's skin, thus precluding the possibility of any compromise of the signal being sensed by reason of a signal leakage to the patient's skin.

Figure 7:
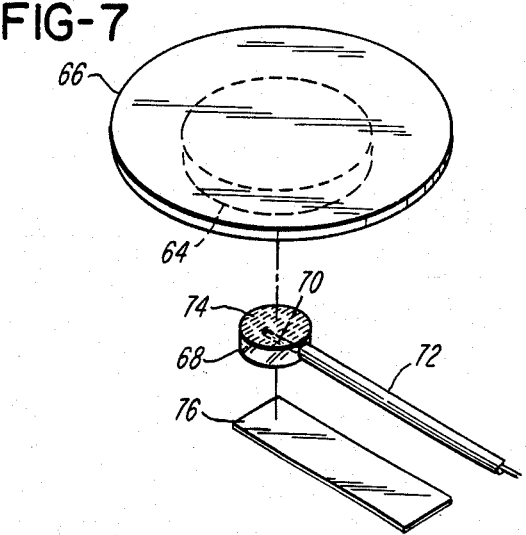
FIG. 7 is a perspective illustration of a third modification of the present invention wherein a reusable conductor assembly and an insulator have been exploded away from a disposable portion of the electrode, a part of the reusable portion having been broken away.

In the third embodiment illustrated in FIG. 7, a body of conductive plastic 68, such as disclosed in U.S. Pat. No. 3,976,055, Monter et al issued Aug. 24, 1976, has insert molded therein a wire 70 which projects outwardly from an insulating sleeve or cover 72. Painted onto the conductive plastic body 68 is a layer 74 comprising a conductive paint such as the already described silver paint.

In use the paint layer 74 is contacted to a conductive adhesive matrix such as the illustrated matrix 64 supported under a cover member 66 and the conductive adhesive material surrounding the painted layer 74 is contacted to the skin of a patient, not shown. This establishes an electrical connection from the patient's skin over the conductive adhesive, over the painted silver layer 74, over the conductive plastic body 68, and from there over the wire 70 which can be engaged by any suitable connector to peripheral equipment.

Since the conductive plastic body 68 may have the signal which it carries compromised by contact with the skin of a patient, this third modification as illustrated in FIG. 7 is protected by a long but narrow insulator 76 which may be rectangular in shape as illustrated in FIG. 7, but may have any other shape desired. The insulator 76 is so located as to lie between the skin of the patient and the conductive plastic body 68.

It is to be understood that insulators such as the insulators 23 and 76 may be utilized in association with any of the electrode devices described in this application to prevent compromise or electrical disturbance of a signal sought to be monitored. Insulating devices such as the insulators 23 and 76 may also be employed wherever desirable to prevent undesired skin contact when signals are being applied.

Although the preferred embodiments of this invention have been described, it will be understood that various changes may be made within the scope of the appended claims.

Having thus described my invention, I claim:

1. A medical electrode for connection to peripheral equipment comprising a disposable portion and a reusable portion, said disposable portion comprising cover means and an electrolyte means having one surface region thereof adhered to one face of said cover means, said reusable portion comprising a metallic part arranged to be removably adhered to a second surface region of said electrolyte means, said metallic part including a lead portion for connection to said peripheral equipment, said electrode adapted for attachment to the skin of a patient by interposing said metallic part between said second surface region and the skin of the patient and by applying a third surface region of said electrolyte means to said skin.

2. The medical electrode of claim 1 wherein said cover means comprises a pliant and imperforate plastic sheet.

3. The medical electrode of claim 2 wherein said cover means further comprises a layer of adhesive disposed on one face of said sheet.

4. The medical electrode of claim 3 wherein said adhesive is a pressure-sensitive adhesive.

5. The medical electrode of claim 1 wherein said electrolyte means comprises a conductive adhesive.

6. The medical electrode of claim 5 wherein said conductive adhesive is a hydrogel.

7. The medical electrode of claim 6 wherein said hydrogel is a urethane hydrogel.

8. The medical electrode of claim 1 wherein said cover means has a surface area substantially exceeding the size of said first surface portion whereby a margin of said cover means lies outside said first surface portion, and including adhesive means for attaching said margin to the skin of said patient.

9. The medical electrode of claim 8 wherein said lead portion is adapted to be interposed between said margin and the skin of said patient and wherein said adhesive means attaches said margin to said lead portion.

10. The medical electrode of claim 1 wherein said metallic part is substantially pure silver.

11. The medical electrode of claim 1 wherein said metallic part comprises substantially pure silver having chlorided surfaces.

12. The medical electrode of claim 11 wherein said lead portion comprises a metal other than silver, and including solder affixing said metal other than silver to said metallic part.

13. The medical electrode of claim 12 wherein said solder is covered by a surrounding sheath.

14. The medical electrode of claim 13 wherein said surrounding sheath is shrink-fitted about said solder.

15. The medical electrode of claim 1 wherein said cover means comprises a pliant sheet and wherein said electrolyte means is located between edge margins of said cover means.

16. The medical electrode of claim 1 wherein said second surface region is small is relation to the third surface region of said electrolyte means.

17. The medical electrode of claim 16 wherein said cover means has a circular edge margin, and said electrolyte means contacts an area of said adhesive spaced within said edge margin.

18. The medical electrode of claim 1 wherein the adhesion of said electrolyte means to said cover means is greater than the adhesion that will occur when said electrolyte means is applied to the skin of a patient and is greater than the adhesion that will occur between said electrolyte means and said metallic part.

19. The medical electrode of claim 1 wherein the opposite face of said cover means is substantially without tack to human skin.

20. The medical electrode of claim 1 wherein said electrolyte means comprises an adhesive rendered conductive by the inclusion of sodium chloride.

21. The medical electrode of claim 1 wherein said electrolyte means comprises an adhesive rendered conductive by the inclusion of a sodium sulphate.

22. The medical electrode of claim 1 wherein said metallic part comprises an electrically conductive paint.

23. The medical electrode of claim 2 wherein said lead portion comprises a strip of non-conductive material painted with said conductive paint.

24. The medical electrode of claim 1 wherein said metallic part comprises an electrically conductive paint adhered to an electrically conductive plastic.

25. The medical electrode of claim 24 including a sheet of non-electrically conductive material interposed between said electrically conductive plastic and the skin of the patient.

26. The medical electrode of claim 1 including a sheet of non-electrically conductive material interposed between said lead portion and the skin of the patient.

27. The medical electrode of claim 1 further including a narrow non-conductive sheet lying over said metallic part and along said lead portion so that said narrow, non-conductive sheet will, when said electrode is attached to the skin of a patient, insulate said metallic part from the skin of the patient without substantially reducing the surface area of said third surface region engagable with the patient's skin.

28. In the method of utilization of a medical electrode comprising a cover means and a conductive adhesive having a first surface region adhered to one face of said cover means, the steps of interposing between the skin of a patient and a second surface region of said conductive adhesive a metallic part having a lead wire adapted for connection to peripheral equipment, and applying a third surface region of said conductive adhesive to the skin of the patient.

* * * * *

UNITED STATES PATENT AND TRADEMARK OFFICE
CERTIFICATE OF CORRECTION

PATENT NO. : 4,832,036

DATED : May 23, 1989

INVENTOR(S) : James V. Cartmell

It is certified that error appears in the above-identified patent and that said Letters Patent is hereby corrected as shown below:

Column 3, line 35, "located" should be --location--.

Column 5, line 43, "optical" should --optional--.

Claim 16, line 2 (column 8, line 4), "is" should be --in--.

Claim 23, line 1 (column 8, line 28), "claim 2" should be--claim 22--.

Signed and Sealed this

Twenty-sixth Day of February, 1991

Attest:

HARRY F. MANBECK. JR.

*Attesting Officer* · *Commissioner of Patents and Trademarks*